United States Patent [19]

Temple, Jr. et al.

[11] 4,361,565
[45] Nov. 30, 1982

[54] 2-[4-[(4,4-DIALKYL-2,6-PIPERIDINEDION-1-yl)BUTYL]-1-PIPERAZINYL]PYRIDINES

[75] Inventors: Davis L. Temple, Jr., Evansville; Joseph P. Yevich, Newburgh; Walter G. Lobeck, Jr., Evansville, all of Ind.

[73] Assignee: Mead Johnson & Company, Evansville, Ind.

[21] Appl. No.: 334,689

[22] Filed: Dec. 28, 1981

[51] Int. Cl.$^3$ .............. C07D 401/14; A61K 31/445; A61K 31/495
[52] U.S. Cl. .................................. 424/250; 544/364; 544/365; 546/242; 546/243
[58] Field of Search ............ 544/364, 365; 546/242, 546/243; 424/250

[56] References Cited

U.S. PATENT DOCUMENTS

| | | | |
|---|---|---|---|
| 3,398,151 | 8/1968 | Wu et al. | 424/250 |
| 3,717,634 | 2/1973 | Wu et al. | 544/230 |
| 3,907,801 | 9/1975 | Wu et al. | 424/250 |
| 3,976,776 | 8/1976 | Wu et al. | 424/251 |
| 4,182,763 | 1/1980 | Casten et al. | 424/251 |
| 4,305,944 | 12/1981 | Temple et al. | 424/250 |

FOREIGN PATENT DOCUMENTS 2023594 1/1980 United Kingdom ............... 544/230

OTHER PUBLICATIONS

Wu et al., Journal of Med. Chem., vol. 15, No. 5, pp. 477-479, 1972.
Wu, et al., Journal of Med Chem., vol. 12, No. 4, pp. 876-881, 1968.
Benica, et al., Journal of the American Pharmaceutical Association, 1950, pp. 451-456.

Primary Examiner—Donald G. Daus
Assistant Examiner—Sharon A. Gibson
Attorney, Agent, or Firm—Richard P. Ryan; Robert H. Uloth

[57] ABSTRACT

1-[4-(4,4-Dialkyl-2,6-piperidinedion-1-yl)butyl]piperazines with 2-2-(3-cyano)pyridyl substituents in the 4-position have been synthesized and demonstrate useful psychotropic properties.

7 Claims, No Drawings

2-[4-[(4,4-DIALKYL-2,6-PIPERIDINEDION-1-YL)BUTYL]-1-PIPERAZINYL]PYRIDINES

BACKGROUND OF THE INVENTION

Related art can be generalized by compounds of the following structural type:

in which n is 4 or 5 and B is a substituted or unsubstituted 2-pyridyl or 2-pyrimidyl moiety. These and related compounds have been prepared as psychotropic agents and are described in:

- Wu, et al., *Journal of Medicinal Chemistry*, 15/5, 477-479 (1972).
- Wu, et al., U.S. Pat. No. 3,717,634 patented Feb. 20, 1973.
- Wu, et al., U.S. Pat. No. 3,907,801 patented Sept. 23, 1975.
- Wu, et al., U.S. Pat. No. 3,976,776 patented Aug. 24, 1976.
- Temple, et al., U.S. Application Ser. No. 184,677 filed Sept. 8, 1980.

Anxiolytic use of one of the above compounds (n=4, B=2-pyrimidyl) which is referred to by the name buspirone, is disclosed by Gasten, et al., U.S. Pat. No. 4,182,763 patented Feb. 8, 1980. Currently, clinical studies to support a submission to U.S. Food & Drug Administration for the use of buspirone in treatment of anxiety neurosis are being conducted.

Another related group of compounds, including some glutarimides but wherein the B substituent is phenyl or substituted phenyl, is disclosed in:

- Wu, et al., U.S. Pat. No. 3,398,151 patented Aug. 20, 1968.
- Wu, et al., *Journal of Medicinal Chemistry*, 12/4, 876-881 (1969).

Of increasing dissimilarity are the compounds of the following structure disclosed by Najer, H., et al., in U.K. patent application No. 7,921,307, published as GB 2,023,594A on Jan. 3, 1980.

These CNS active compounds are described as being useful in treatment of anxiety and depression.

A piperidyl compound of the following structure was reported by Pollard, et al., in *The Journal of Organic Chemistry*, 24/6, 764-767 (1959); but no utility was given.

Finally, related but not closely, are some 3,3-dialkylglutarimides as shown in the following structure and reported by Benica, et al., *Journal of the American Pharmaceutical Association*, 1950, 451-456.

where $R^1$ is $C_1$ to $C_4$ alkyl and $R^2$ is H or $C_1$ to $C_4$ alkyl. Pharmacological testing of these glutarimides did not reveal any useful physiological activity of significance.

SUMMARY OF THE INVENTION

This invention is concerned with a new series of CNS-active compounds characterized by the following general structural formula (I)

and the non-toxic pharmaceutically acceptable acid addition salts thereof. In the foregoing formula $R^1$ and $R^2$ are independently selected from $C_1$ to $C_4$ alkyl groups; and Z can be hydrogen; halogen or pseudohalogen, preferably fluoro, chloro, or trifluoromethyl.

The instant compounds differ most notably from buspirone and its related analogs in that their spiroalkylene moiety has been replaced by geminal dialkyl groups.

Testing in biological model systems have shown the compounds of the instant invention to be psychotropic agents possessing actions indicative of anxiolytic and antipsychotic activities.

DETAILED DESCRIPTION OF THE INVENTION

Synthetic methods employed for preparation of Formula I compounds are described in the above cited U.S. Pat. Nos. 3,907,801 and U.S. application Ser. No. 184,677. These methods may be adapted to variation in order to produce other compounds embraced by this invention but not specifically disclosed. Variations of the methods to produce the same compounds in somewhat different fashion will also be evident to one skilled in the art. Certain examples will be given for specific illustration.

A unitary process, combining the various preparative methods (A, B and C) which can be used, is depicted below. Methods B and C are preferred for synthesis of the subject compounds.

Unitary Process

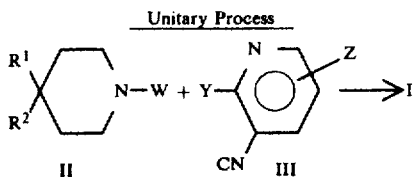

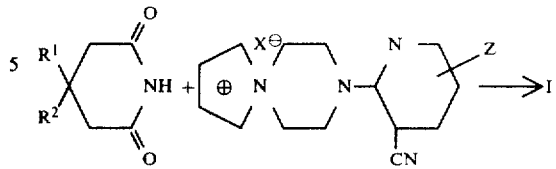

In this scheme, R¹, R², and Z have the same meanings as previously assigned to them in Formula I. The symbol "W" can be H; or

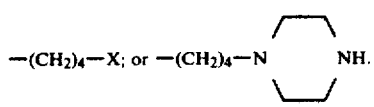

The symbol "Y" can be

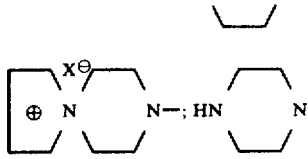

The relationship between W and Y is:

Method B

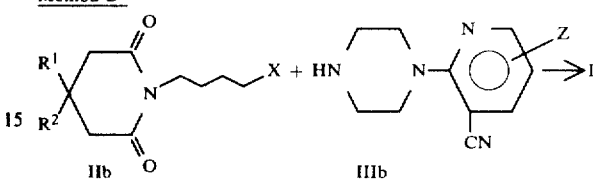

Method C

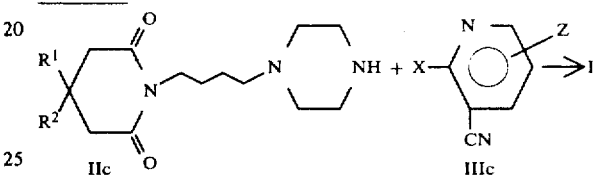

For methods A through C, the process is carried out under reaction conditions suitable for the preparation of tertiary amines by alkylation of secondary amines. The

| Method No. | A | B | C |
|---|---|---|---|
| when W is: | H (IIa) | —(CH₂)₄—X (IIb) | —(CH₂)₄—N⌒NH (IIc) |
| then Y is: | X—(CH₂)₄—N⌒N— (IIIa) | [⊕N⌒N—]X⊖ (IIa') | HN⌒N— (III) | X (IIIc) |

The symbol "X" refers to a suitable displacement group such as chloride, bromide, iodide, sulfate, phosphate, tosylate, or mesylate.

Method A

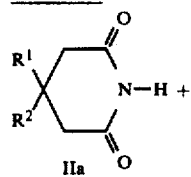

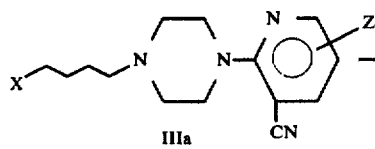

reactants are heated in a suitable organic liquid at temperatures of about 60° C. to about 150° C. in the presence of an acid binding agent. Benzene, dimethylformamide, ethanol, acetonitrile, toluene, and n-butyl alcohol are preferred examples of the organic liquid reaction media. The preferred acid binding agent is potassium carbonate, but other inorganic and tertiary organic bases may be employed including other alkali and alkylene earth metal carbonates, bicarbonates, or hydrides, and the tertiary amines. All three methods have been adequately described in the application of Temple, et al and by Wu, et al in the cited patents and articles listed above and these are hereby incorporated in entirety by reference.

The intermediate dialkyl glutaric acid anhydrides or imides of Formula II are commercially available, found in the chemical literature, or described herein. The general synthesis of these compounds is illustrated in Scheme 1.

Scheme 1

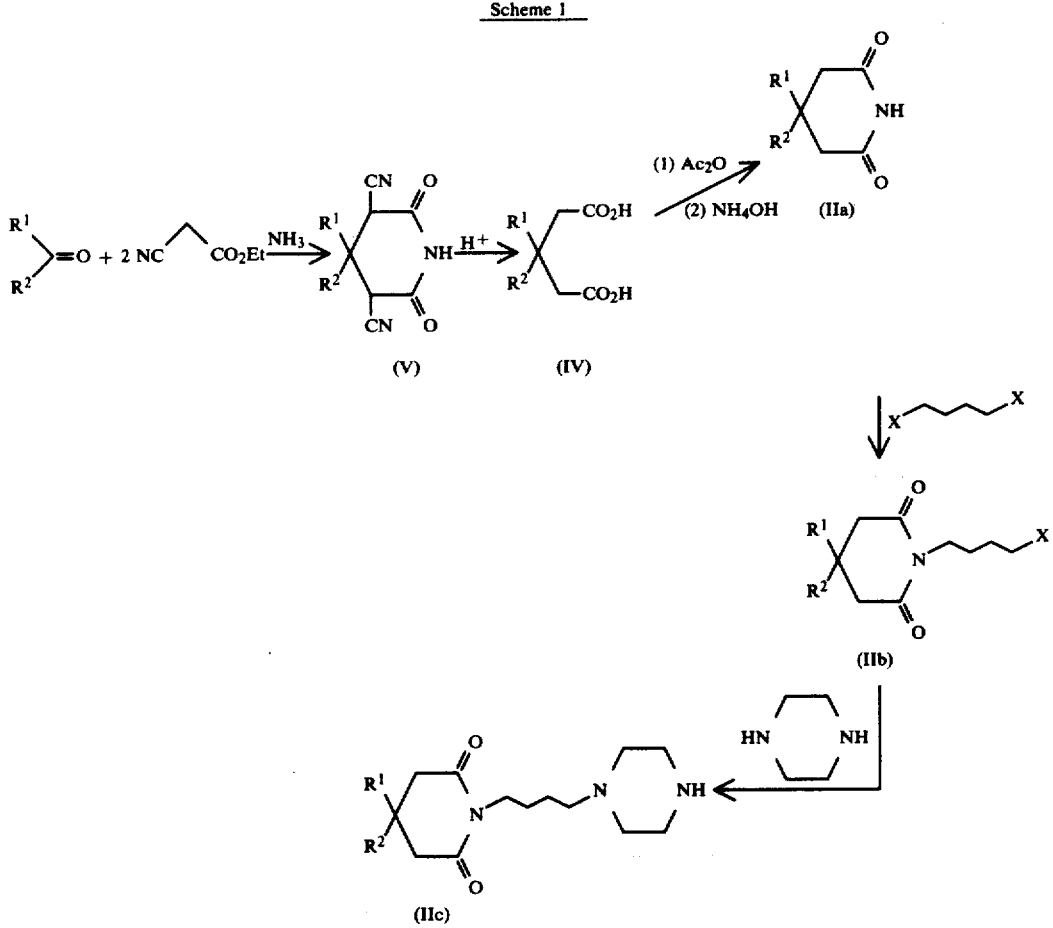

In the above scheme, $R^1$, $R^2$ and X are the same as defined hereinabove. The general synthesis is carried out by stirring a chilled mixture of 1 equivalent of the ketone with 2 equivalents of ethylcyanoacetate in an inert organic solvent containing dissolved gaseous ammonia. After stirring the chilled reaction mixture for 24 to 48 hours, the 2,4-dicyanoglutarimide product (V) is obtained and is hydrolyzed in strong mineral acid to the dicarboxylic acid product (IV). Dehydration with acetic anhydride yields the dialkylglutaric acid anhydride (IIa) which in turn can be converted to the dialkylglutarimide (IIb) by treating with ammonium hydroxide under dehydrating conditions. The N-substituted glutarimide (IIc) is readily obtained by treating (IIb) with an appropriate 1,4-disubstituted butane, e.g. 1,4-dibromobutane.

The pyridine intermediates (III) are described in the aforementioned Temple, et al. and Wu, et al. references, cited above. Although these procedures are applicable to the preparation of other pyridine intermediates not specifically disclosed therein but which are required as intermediates for the present invention, representative syntheses of III are given as working examples for further exemplification. Intermediates IIIa or IIIa' and IIIb are readily obtainable from IIIc using the standard methods shown by Wu, et al. and by Temple, et al., supra. Some IIIc pyridines are commercially available.

Synthesis of (III)

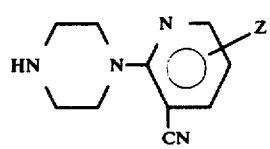

Synthesis of (III)

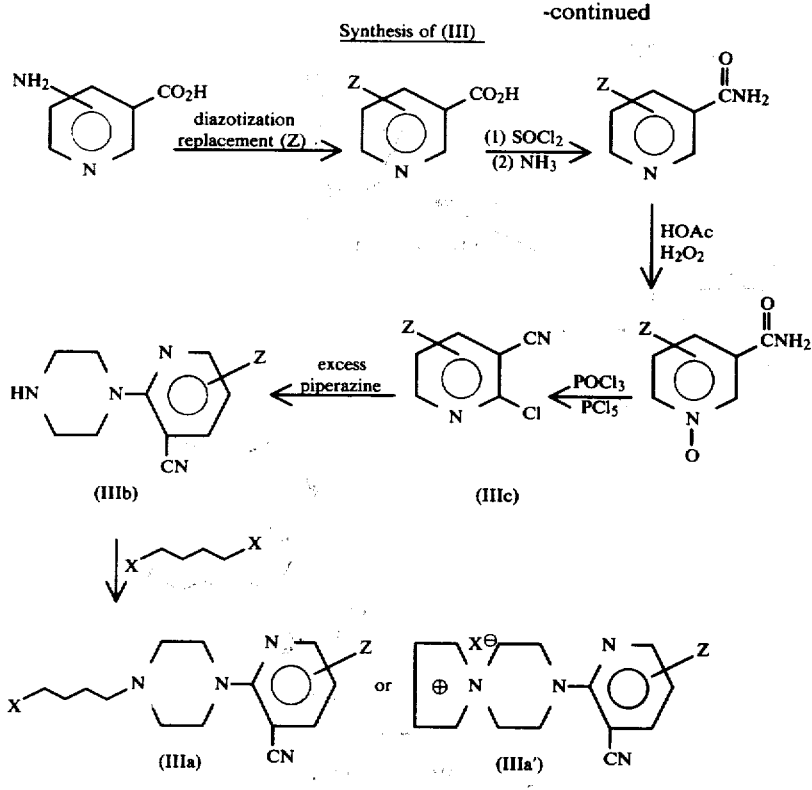

Z is halogen or pseudohalogen.

This synthetic scheme begins with a commercially available aminonicotinic acid and proceeds by known organic reactions via the nicotinamide and ultimately to the pyridine intermediates.

The formula (I) compounds are useful psychotropic agents which exhibit antipsychotic and anxiolytic actions.

The following screening tests were utilized as the basis to determine the psychotropic actions of the instant compounds. These tests comprise:

1. Conditioned avoidance response in fasted rats treated orally. These data were obtained by the methods described in the Wu, et al. patents and publications described hereinabove.
2. Dopamine receptor binding assay reflecting antipsychotic activity (Burt, Crease, and Synder, *Molecular Pharmacology*, 12:800 (1976); Burt, Crease, and Synder, *Science*, 196:326 (1977); Crease, Burt, and Snyder, *Science*, 192:481 (1976).
3. Apomorphine stereotype behavior test in non-fasted rats which determines the ability of centrally active compounds to block apomorphine induced stereotype behavior. This preclinical test is an indication of potential antipsychotic efficacy (Janssen, et al., Arzneimittel-Forsch., 17:841 (1966)).

The compounds of the present invention show good activities in these tests. Additionally, these compounds are inactive at oral doses of 200 mg/kg in the rat catalepsy test (Costall and Naylor, *Pyschopharmacologica*, 34:233 (1974) signifying low potential for undesired extrapyramidal side-effects.

According to the pharmacological profile established by the aforementioned tests, these compounds of Formula (I) have promising potential as antipsychotic/anxiolytic agents. Thus, another aspect of the instant invention concerns a process for ameliorating an anxiety or psychotic state in a mammal in need of such treatment which comprises systemic administration to said mammal of an effective dose of about 0.01 to 40 mg/kg body weight of a formula (I) compound or a pharmaceutically acceptable acid addition salt thereof.

The term system administration as used herein refers to oral, rectal, and parenteral (i.e., intramuscular, intravenous, and subcutaneous) routes. Generally, it will be found that when a compound of the present invention is administered orally, which is the preferred route; a larger quantity of the active agent is required to produce the same effect as a smaller quantity given parenterally. In accordance with good clinical practice, it is preferred to administer the instant compounds at a concentration level that will produce effective antipsychotic/anxiolytic effects without causing any harmful or untoward side effects.

Therapeutically, the instant compounds are generally given as pharmaceutical compositions comprised of an effective antipsychotic/anxiolytic amount of a compound of Formula (I) or a pharmaceutically acceptable acid addition salt thereof and a pharmaceutically acceptable carrier. Pharmaceutical compositions which provide from about 1 to 500 mg of the active ingredient per unit dose are preferred and are conventionally prepared as tablets, lozenges, capsules, powders, aqueous or oily suspensions, syrups, elixirs and aqueous solutions.

Preferred oral compositions are in the form of tablets or capsules and may contain conventional excipients such as binding agents (e.g. syrup, acacia, gelatin, sorbitol, tragecanth, or polyvinyl pyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch), and wetting agents (e.g. sodium lauryl sulfate). Solutions or suspension of a Formula (I) compound with conventional pharmaceutical vehicles are employed for parenteral compositions such as an aqueous solution for intravenous injection or an oily suspension for intramuscular injection. Such compositions having the desired clarity, stability and adaptability for parenteral use are obtained by dissolving from 0.1% to 10% by weight of the active compound in water or a vehicle consisting of a polyhydric aliphatic alcohol such as glycerine, propyleneglycol, and polyethyleneglycols or mixtures thereof. The polyethyleneglycols consist of a mixture of non-volatile, normally liquid, polyethyleneglycols which are soluble in both water and organic liquids and which have molecular weights from about 200 to 1500.

DESCRIPTION OF SPECIFIC EMBODIMENTS

The compounds which constitute this invention and their methods of preparation will appear more fully from a consideration of the following examples which are given for the purpose of illustration only and are not to be construed as limiting the invention in sphere or scope. All temperatures are understood to be in °C. when not specified.

SYNTHESIS OF INTERMEDIATES

EXAMPLE 1

3-Methyl-3-n-propylglutarimide (IIa)

(a) 2,4-dicyano-3-methyl-3-n-propylglutarimide (V). A mixture of 107.8 g (1.25 moles) of 2-pentanone, 282.8 g (2.5 moles) of ethyl cyanoacetate and 650 mL of anhydrous ethanol containing approximately 45 g of dissolved ammonia gas was stirred for 48 hr while being kept at 0° C. The crude product was removed by filtration, redissolved in hot water and acidified with conc. HCl resulting in precipitation of a white solid which was isolated by filtration to give 218.7 g (80%) of material which, upon recrystallization from ethanol, had a melting point of 204°–205° C.

(b) 3-Methyl-3-n-propylglutaric Acid (IV). The glutarimide (V); (225 g, 1.02 moles) was added in portions to 480 mL conc. $H_2SO_4$. The resulting orange solution was stirred for 12 hr and then diluted by the slow addition of 420 mL $H_2O$. Carbon dioxide evolution began immediately. Following completion of the addition of water, the mixture was gradually heated, to minimize excessive foaming, up to reflux. Gas evolution ceased after 5 hr of reflux and the reaction mixture was diluted with 1 L water, saturated with NaCl, and extracted three times with 600 mL portions of ether. The ether extracts were dried ($Na_2SO_4$), filtered and concentrated to a residual yellow syrup which solidified to give 88 g of the crude diacid product, melting point 90°–92° C.

A 70 g (0.37 mole) portion of this crude glutaric acid (IV) was dissolved in 110 mL of acetic anhydride and gently refluxed for a period of 4 hr. The solution was concentrated to a dark oil which was distilled to give 53.2 g (84.5%) of colorless syrup, boiling point 111° at 0.1 mm.

A 10 g (0.06 mole) quantity of this syrup was added in small portions to 120 mL conc. $NH_4OH$. After the addition was completed, the mixture was heated to a gentle reflux and stirred for 4 hr. Upon cooling the reaction mixture, a yellow oil precipitated which solidified to a glass. Crystallization of the glass from isopropyl alcohol gave 8 g (80%) of crude product, m.p. 110°–112° C. (literature m.p. 115°–116°, Cf: N. S. Benica and C. O. Wilson, *J. Am. Pharm. Assoc.*, 39, page 451-454 (1950)).

EXAMPLE 2

N-(4-Bromobutyl)-3-methyl-3-n-propylglutarimide (IIb)

A mixture of the IIa product prepared in Example 1 (25 g; 0.15 mole), 1,4-dibromobutane (33.5 g; 0.15 mole), and $K_2CO_3$ (40.6 g; 0.29 mole) was stirred for a period of 16 hrs in 250 mL refluxing acetonitrile. The inorganic solid was removed by filtration and the filtrate was concentrated to a oil which was distilled to give 42.5 g (95%) of a light yellow oil, b.p. 165°–190° at 0.09 mm.

EXAMPLE 3

N-[4-(1-Piperazinyl)butyl]-3,3-dimethylglutarimide (IIc)

A mixture of N-(4-bromobutyl)-3,3-dimethylglutarimide (20.0 g; 0.07 mole [prepared from 3,3-dimethylglutarimide using the method of Example 2]); piperazine (31.0 g; 0.36 mole); $K_2CO_3$ (29.8 g; 0.22 mole); and KI (0.1 g) was refluxed in 250 mL acetonitrile for 18 hr. The mixture was filtered, concentrated and the unreacted piperazine removed by vacuum sublimation. The residual material was distilled to yield 17.2 g (85%) product, b.p. 170°–178° C. at 0.01 mm.

EXAMPLE 4

8-(2-(3-Cyano)pyridinyl-8-aza-5-azoniaspiro[4.5]decane Bromide (IIIa')

A mixture of 1-[2-(3-cyano)pyridinyl]piperazine (37.4 g; 0.2 mole), 1,4-dibromobutane (108 g; 0.5 mole) and finely powdered sodium carbonate (21.2 g, 0.2 mole) in 400 mL isopropanol was stirred and refluxed for a 16 hr period. The hot reaction mixture was filtered and the filtrate, on standing at room temperature, provided 50 g (80% yield) of product.

(The open chain intermediate, 1-(4-bromobutyl)-4-(2-(3-cyano)pyridinyl)piperazine (IIIa), can be synthesized according to methods described by Wu, et al, U.S. Pat. No. 3,717,634 or Pollard, et al., *Journal of Organic Chemistry*, Vol. 24, page 764–7 (1959)).

EXAMPLE 5

1-(3-Cyano-2-pyridinyl)piperazine (IIIb)

2-Chloro-3-cyanopyridine (5.5 g; 0.04 mole) was dissolved in 80 mL ethanol (warming) and piperazine (17.2 g; 0.2 mole) was combined with this solution and the whole stirred at room temperature for 18 hrs. The reaction mixture was filtered and the filtrate concentrated to a residue which was partitioned between $Et_2O$ and $H_2O$. The water layer was made basic and extracted with $Et_2O$. The $Et_2O$ extracts were washed with water, dried ($MgSO_4$), concentrated to a solid which was recrystallized from Skellysolve B to yield 3.2 g product, m.p. 102°–104° C.

Other IIIb intermediates can be made similarly by selection of appropriately substituted 2-chloro-3-cyanopyridines. These are commercially available, described in the chemical literature, or can be made from nicotinic acids or amides as shown schematically hereinabove.

Synthesis of Products (I)

In the examples which follow, melting points, unless specified otherwise, are uncorrected. The nuclear magnetic resonance (NMR) spectral characteristics refer to chemical shifts (δ) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), multiplet (m), doublet (d), triplet (t), quartet (q), or doublet of doublets (dd). Coupling intervals in Hz resulting from peak splitting by adjacent protons are given in brackets. Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed using potassium bromide (KBr) as diluent. The elemental analyses are reported as percent by weight.

EXAMPLE 6

2-[4-[4-(4-Methyl-2,6-dioxo-4-propyl-1-piperadinyl)-butyl]-1-piperazinyl]-3-pyridinecarbonitrile A mixture of N-(4-bromobutyl)-3-methyl-3-n-propyl-glutarimide (3.70 g; 0.012 mole); 2-(1-piperazinyl)-3-pyridinylcarbonitrile (2.29 g; 0.012 mole); $K_2CO_3$ (1.68 g; 0.012 mole); and NaI (0.90 g; 0.006 mole) were combined in approximately 125 mL acetonitrile and refluxed for 12–18 hr. The reaction mixture was filtered and concentrated in vacuo to a residual oil which was partitioned between chloroform and water. The chloroform layer was dried (MgSO$_4$) and concentrated to an oil which was taken up in ethyl ether and converted to the tosylate salt using a minimal amount of acetonitrile. Filtration of the tosylate salt gave 3.0 g white solid, m.p. 146.5°–149° C.

Anal. Calcd. for $C_{23}H_{33}N_5O_2 \cdot 2C_7H_8O_3s$: C, 58.79; H, 6.54; N, 9.27. Found: C, 58.47; H, 6.60; N, 8.98.

NMR (DMSO-$d_6$): 0.86 (3,m); 0.94 (3,s); 1.25 (2,m); 1.56 (6,m); 2.30 (6,s); 2.53 (4,s); 3.19 (4,m); 3.60 (6,m); 4.27 (2,bd [13.0 Hz]); 7.11 (3,m); 7.54 (2,m); 8.16 (1,dd [1.8, 7.5 Hz]); 8.47 (1,dd [1.8, 4.7 Hz]); 9.67 (1,bs); 11.00 (1,bs).

IR (KBr): 815, 1010, 1030, 1120, 1165, 1225, 1350, 1435, 1555, 1620, 1670, 1720, 2230, and 2960 cm$^{-1}$.

EXAMPLE 7

2-[4-[4-(4,4-Diethyl-2,6-dioxo-1-piperidinyl)butyl]-1-piperazinyl]-3-pyridinecarbonitrile Hydrochloride N-(4-Bromobutyl)-3,3-diethylglutarimide (3.4 g; 0.012 mole), 1-(3-cyano-2-pyridinyl)piperazine (2.3 g; 0.012 mole), $K_2CO_3$ (1.7 g; 0.012 mole), and NaI (1.8 g; 0.012 mole) were reacted in acetonitrile in the manner described in Example 6 above. Work up of the product as the hydrochloride salt yielded 1.1 g off-white solid, m.p. 134°–139° C.

Anal. Calcd. for $C_{23}H_{33}N_5O_2 \cdot HCl$: C, 61.67; H, 7.66; N, 15.64. Found: C, 61.41; H, 7.56; N, 15.54.

NMR (DMSO-$d_6$): 0.79 (6,t [7.2]); 1.32 (4,q) [7.2]); 1.65 (4,m); 2.55 (4,s); 3.14 (4,m); 3.67 (6,m); 4.28 (2,bd [13.2]); 7.06 (1,dd [4.8, 7.8]); 8.17 (1,dd [1.6, 7.8]); 8.48 (1,dd [1.6, 4.8]); 11.90 (1,bs).

IR (KBr): 1120, 1360, 1440, 1555, 1585, 1670, 1720, 2210, 2450, and 2965 cm$^{-1}$.

EXAMPLE 8

2-[4-[4-(4,4-Dimethyl-2,6-dioxo-1-piperidinyl)butyl]-1-piperazinyl]-3-pyridinecarbonitrile Hydrochloride Hydrate Following the procedure given in Example 6, N-(4-bromobutyl)-3,3-dimethylglutarimide (2.0 g; 0.007 mole), 1-(3-cyano-2-pyridinyl)-piperazine (1.4 g; 0.007 mole), $K_2CO_3$ (1.1 g; 0.008 mole), and KI (0.1 g) gave 1.5 g of off-white solid, m.p. 185°–190° C. (dec).

Anal. Calcd. for $C_{21}H_{29}N_5O_2 \cdot 1.6HCl \cdot 0.25$ $H_2O$: C, 56.51; H, 7.02; N, 15.69; Cl, 12.71. Found: C, 56.85; H, 6.89; N, 15.65; Cl, 12.89.

NMR (DMSO-$d_6$): 1.00 (6,s); 1.60 (4,m); 2.56 (4,s); 3.10 (4,m); 3.64 (6,m); 4.25 (2,bd [13.0]); 7.06 (1,dd [4.6, 7.5]); 8.17 (1,dd) [1.8, 7.5]); 8.50 (1,dd [1.8, 4.6]); 9.50 (1,bs).

IR (KBr): 1125, 1350, 1440, 1550, 1605, 1620, 1670, 1720, 2212, 2400, and 2960 cm$^{-1}$.

The following products of Formula I can be prepared using the appropriate glutarimide and pyridinylpiperazine in the procedure of Example 6.

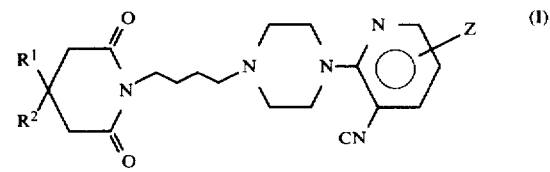

| Example | $R^1$ | $R^2$ | Z |
|---|---|---|---|
| 9 | Et | Me | H |
| 10 | n-Bu | Me | 5-F |
| 11 | Et | Et | 5-Cl |
| 12 | Me | Me | 5-CF$_3$ |
| 13 | Et | Et | 5-F |
| 14 | n-Pr | Me | 5-F |

What is claimed is:

1. A compound selected from the group consisting of a compound having Formula (I)

wherein
$R^1$ and $R^2$ are independently selected from $C_1$ to $C_4$ alkyl groups; with Z being hydrogen; halogen or pseudohalogen, preferably fluoro, chloro, or trifluoromethyl
and the non-toxic pharmaceutically acceptable acid addition salts thereof.

2. A compound of claim 1 wherein Z is 5-fluoro.

3. The compound of claim 1, 2-[4-[4-(4,4-dimethyl-2,6-dioxo-1-piperidinyl)butyl]-1-piperazinyl]-3-pyridincarbonitrile or a pharmaceutically acceptable acid addition salt thereof.

4. The compound of claim 1, 2-[4-[4-(4,4-diethyl-2,6-dioxo-1-piperidinyl)butyl]-1-piperazinyl]-3-pyridincarbonitrile or a pharmaceutically acceptable acid addition salt thereof.

5. The compound of claim 1, 2-[4-[4-(4-methyl-2,6-dioxo-4-propyl-1-piperidinyl)butyl]-1-piperazinyl]-3-pyridincarbonitrile or a pharmaceutically acceptable acid addition salt thereof.

6. The process for ameliorating an undesirable anxiety/antipsychotic state in a mammal comprising systemic administration to said mammal of an effective psychotropic dose of from 0.01 to 40 mg/kg body weight of a Formula (I) compound or a pharmaceutically acceptable acid addition salt thereof.

7. A pharmaceutical composition in dosage unit form suitable for systemic administration to a mammalian host comprising a pharmaceutical carrier and an amount of a Formula (I) compound to provide an effective non-toxic dose of from 0.01 to 40 mg/kg body weight of said host.

* * * * *